Figure 1:
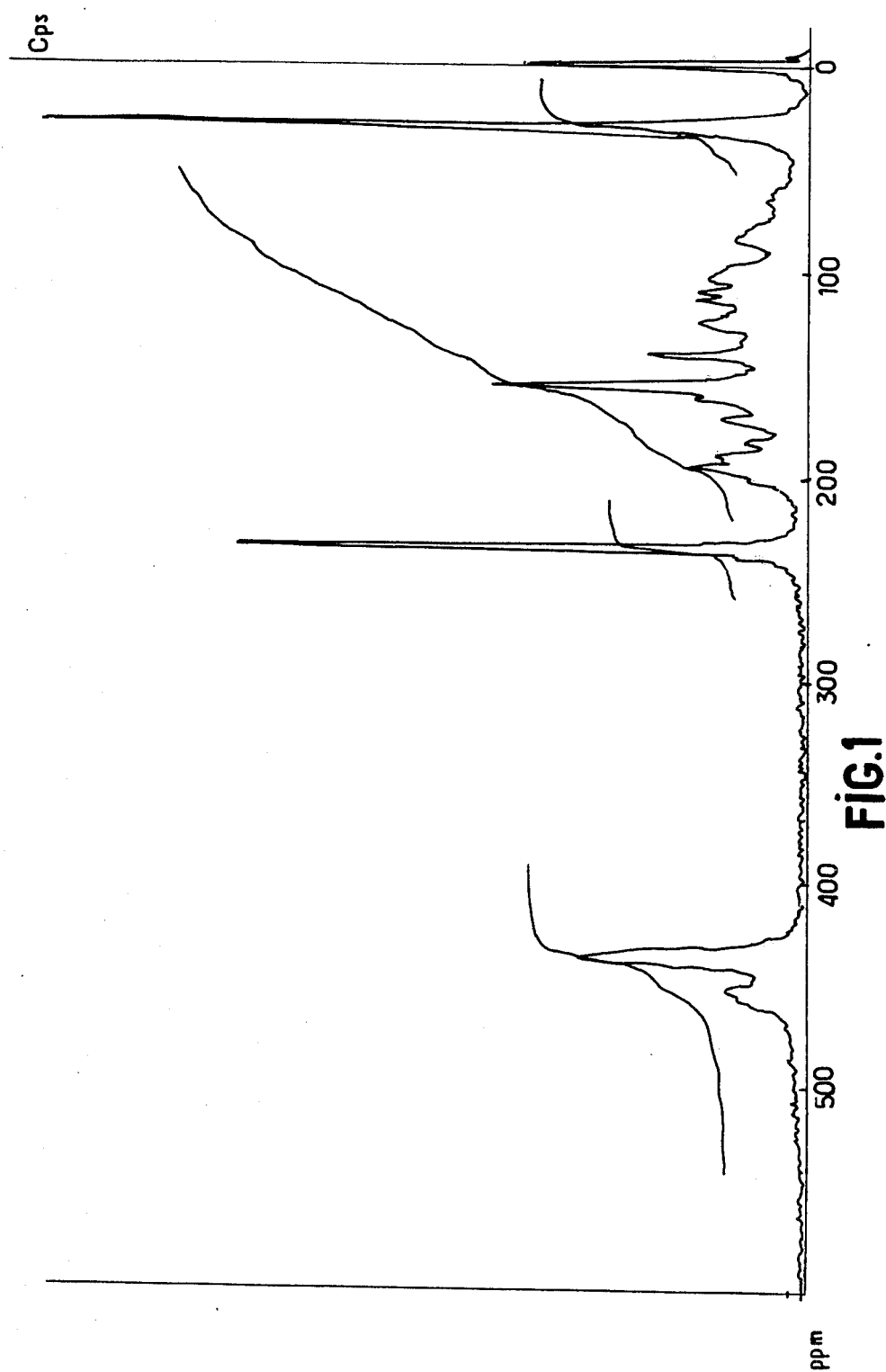

United States Patent [19]

Heymes

[11] 4,152,519
[45] May 1, 1979

[54] 16-HYDROXY ASPIDOSPERMIDINES AND A PROCESS FOR THEIR PRODUCTION

[75] Inventor: Alain Heymes, Portet, France

[73] Assignee: Parcor, Paris, France

[21] Appl. No.: 813,670

[22] Filed: Jul. 7, 1977

[30] Foreign Application Priority Data

Jul. 13, 1976 [FR] France ................. 76 21431

[51] Int. Cl.$^2$ ......................... C07D 471/16
[52] U.S. Cl. ..................... 546/51; 424/258
[58] Field of Search ............ 260/287 B, 287 P; 546/51

[56] References Cited
U.S. PATENT DOCUMENTS 3,894,028  7/1975  Levy ................. 260/287 P
3,987,048  10/1976  Le Men et al. ......... 260/287 P

OTHER PUBLICATIONS

Morrison et al., Organic Chemistry, 1966, pp. 859–860, 161–162.
House, Modern Synthetic Reactions, 1965, pp. 92–93.

Primary Examiner—Donald G. Daus
Assistant Examiner—David E. Wheeler
Attorney, Agent, or Firm—Cushman, Darby & Cushman

[57] ABSTRACT

This invention relates to novel aspidospermidines being useful in synthesis and also exhibiting interesting physiological properties. A process for the preparation of the novel compounds is described and exemplified and examples of pharmaceutical compositions containing the novel compounds are given. Pharmacological test data are presented for a novel compound according to the invention.

7 Claims, 2 Drawing Figures

16-HYDROXY ASPIDOSPERMIDINES AND A PROCESS FOR THEIR PRODUCTION

This invention relates to indole compounds. It relates more particularly to new aspidospermidines, a process for their preparation, and their use, particularly in therapy.

French Patent Specifications Nos. 2,133,649 and 2,155,265 describe the preparation of certain aspidospermidines using lead tetraacetate (for the 16-acetoxy compound) and an alkyl hypochlorite (for the 16-chloro derivative) respectively. Formulae for 16-hydroxy or 16-alkoxy compounds have also been proposed on paper. It was even mentioned that the action of oxygen in the presence of a catalyst such as $PtO_2$ on the starting vincadiformine or tabersonine results in these compounds. However, there is no mention of a detailed method for obtaining the hydroxy compound, nor that its physical properties and the described rearrangement of the 4-N-oxides show that this unconventional synthesis by oxidation in the presence of $PtO_2$ is impracticable, as has been shown by unsuccessful tests which we have carried out and by the third paragraph of the article by Georgette Hugel et al, C.R. Acad. Sc. Paris, vol. 274 (Apr. 5, 1972) one of the collaborators of which was the inventor for French Pat. Nos. 2,133,649 and 2,155,265.

However, the value of the hydroxy compounds as intermediates in synthesis is beyond a doubt, and other researchers have believed that they have formed these compounds, at least temporarily, without isolating them, in a semi-synthesis resulting in vincamine. Thus, in Belgian Patent Specification No. 832,157 (page 6, lines 7 to 10) the hypothesis is presented that the reaction conditions permit the formation of the 16-hydroxy derivative, but without having an oxidising effect on the nitrogen atom in the 4-position, or else without forming the 16-hydroxy-N-oxy compound. The reaction is effected in an acidic medium (page 6, line 2). We have prepared and isolated the 16-hydroxy compound, and as it is unstable in an acidic medium, it is clear that this process cannot constitute a method of preparing the compound in question.

According to one feature of the present invention there are provided aspidospermidines of formula

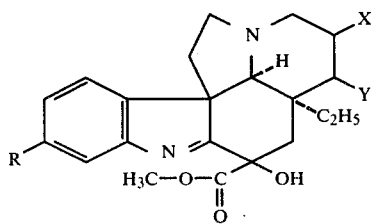

(wherein R is hydrogen or methoxy, and X and Y are hydrogen or together represent a double bond between the carbon atoms to which they are attached).

According to a further feature of the invention there is provided a process for preparing these aspidospermidines comprising converting the amines of formula:

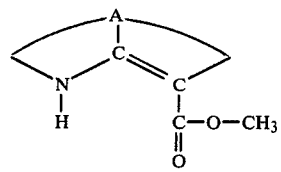

into their carbanions of formula:

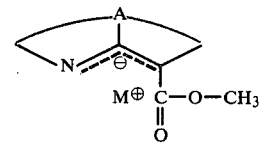

(wherein M is an alkali metal or alkaline earth metal ion), oxidising the carbanion with oxygen into the hydroperoxide of formula:

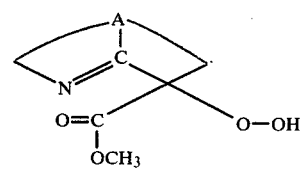

and reducing this hydroperoxide. In the above formulae A represents the trivalent radical

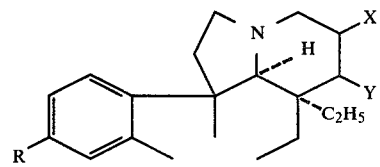

(wherein R, X and Y are as hereinbefore defined).

In this way is it possible to selectively oxidise and so prepare the pure hydroxy compound without forming N-oxides.

The first stage of the process comprises forming the carbanions. For this purpose, a base is used, such as an alkali metal hydride, preferably sodium, lithium or potassium hydride; an alkali metal amide or alkylamide, advantageously a dialkylamide having up to 12 carbon atoms; or an alkali metal alkylsilylamide, especially lithium- and sodium-bis (trialkylsilyl)-amide. As the base, alkali metal or alkaline earth metal alkoxides may also be used, such as, for example, sodium methoxide, potassium methoxide, magnesium methoxide, potassium t-butoxide and sodium t-pentoxide.

The base is generally used in a slight excess, for example 10% excess based on the stoichiometric quantity.

The process is generally carried out at temperatures between $-78°$ C. and $+50°$ C., lower temperatures being preferred. Generally, the reaction takes from 5 minutes to 12 hours.

The preferred solvents are dimethylformamide, the dimethylsulphoxide of 4- to 8-membered heterocyclic compounds interrupted by an oxygen atom, such as tetrahydrofuran, hydrocarbons, especially alkanes, alcohols, amides, aromatic hydrocarbons such as benzene, toluene and xylenes.

The second stage of the process comprises oxidising the carbanion to the hydroperoxide. Oxygen is used at a pressure of 1 to 10 kg.cm$^{-2}$ conveniently for 5 minutes to 12 hours. The reaction proceeds satisfactorily at temperatures between −30° C. and +50° C.

The oxygen may be a mixture of oxygen and an inert gas such as nitrogen or a noble gas.

The third stage of the process comprises reducing the hydroperoxide into the corresponding 16-hydroxy compound. This may conveniently be carried out with reducing agents such as for example alkylphosphites, especially trialkylphosphites, alkali metal borohydrides or salts at the lower state of oxidation, such as the stannous or ferrous chlorides, etc. This reduction proceeds satisfactorily at temperatures between −30° and +50° C.

An example of the preparation of the aspidospermidines according to the invention is given hereinafter.

1,2-Dehydro-16-carbomethoxy-16-hydroxy-aspidospermidine
(i.e. $R = X = Y = H$)

At ambient temperature, a solution of 33.8 g (0.1 mol) of (−)-vincadiformine in a mixture of 140 ml of anhydrous dimethylformamide (DMF) and 140 ml of anhydrous toluene is added, over a period of 30 minutes, to a suspension of 2.64 g (0.11 mol) of sodium hydride in a mixture of 200 ml of anhydrous tetrahydrofuran and 20 ml of anhydrous hexamethyl phosphotriamide (HMPT). When the release of hydrogen has ceased (about two hours later), the solution is cooled to −10° C. then agitated in an oxygen atmosphere until no further oxygen is absorbed (duration; 3 hours). Then 18.7 ml (0.14 mol) of trimethylphosphite are added.

After addition of 300 ml of water, the mixture is extracted with methylene chloride. The organic phase, dried over calcium chloride and evaporated, yields 30 g of crude product. By chromatographing this product on a 750 g silica gel column, 9 g of the pure product desired are obtained in crystalline form (yield: 25%).

M.p.: 124° C.
$[\alpha]_D^{31}$: −154° (c=1, chloroform)
i.r. (KBr): δOH at 3500 cm$^{-1}$
δc=0 to 1750 cm$^{-1}$
n.m.r. (CDCl$_3$): 0.5 ppm (5H)
(compared with TMS) 3.9 ppm (3H)

Figure 2:
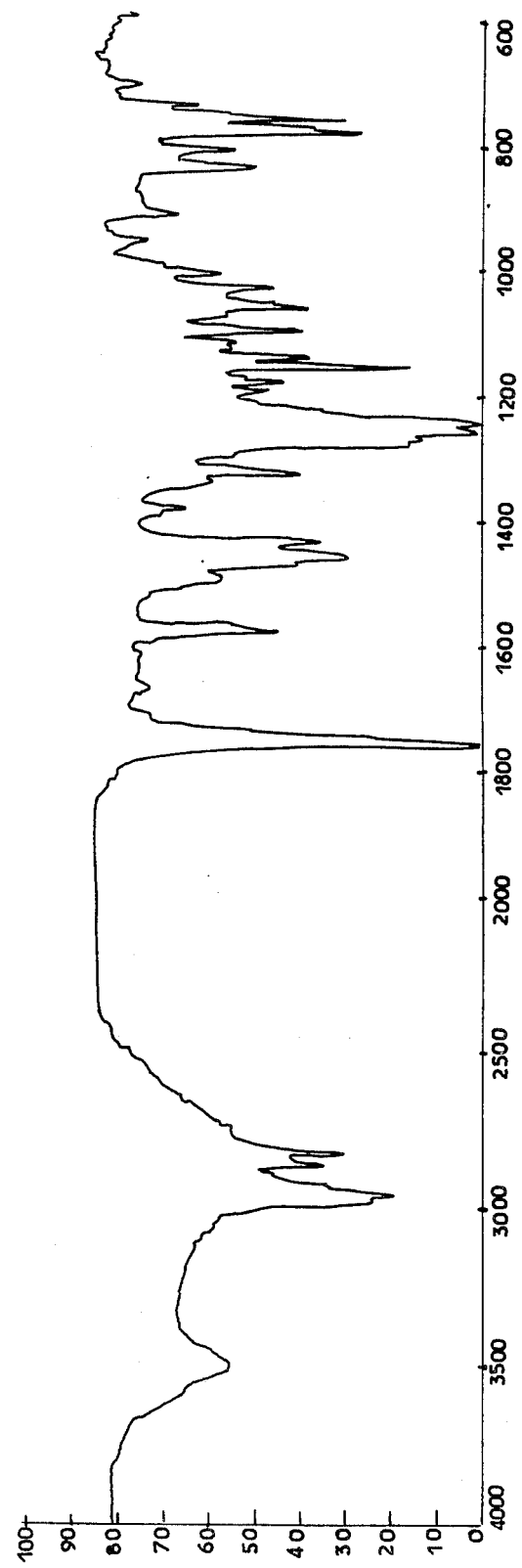

The n.m.r. and i.r. spectra of this product are given in FIGS. 1 and 2 respectively.

Analysis: C$_{21}$H$_{26}$N$_2$O$_3$. Calculated %: C 71.15; H 7.39; N 7.90. Found %: C 71.12; H 7.42; N 7.75.

The aspidospermidines according to the invention may be converted into vincamine, 16-epivincamine; 14, 15-dehydrovincamine; 14,15-dehydro-16-epivincamine and the corresponding vincine derivatives thereof (R=methoxy) by treating in an acidic medium as described, for example, in the afore-mentioned French patents. Since the compounds according to the invention may be converted into vincamine derivatives, e.g. by catalytic hydrogenation, they are valuable synthesis intermediates.

Moreover, the compounds according to the invention themselves have interesting therapeutic properties, as indicated by the toxicological and pharmacological studies reported below for the compound prepared in the preceding Example.

I - TOXICOLOGICAL STUDY

This study dealt with
1. the acute toxicity,
2. the chronic toxicity (rats and dogs),
3. the delayed toxicity,
4. the local and general tolerance,
5. the possible teratogenic effects, and showed that the compound is tolerated well both orally and by parenteral or intramuscular route, without causing local or general reactions.

The results of the study of the acute toxicity were as follows, the tests having been carried out on the mouse and rat, whilst the product was administered intravenously, subcutaneously and by oesophageal tube. The doses studied were administered in a volume of 1 ml/100 g of body weight, whilst each dose was administered to 5 males and 5 females; the LD 50 was investigated using the SPEARMAN-KARBER method.

| Species of animal | Route of administration | LD50/72 hrs/mg/kg |
|---|---|---|
| mouse | i.v. | 86.0 |
|  | s.c. | 175.7 |
|  | p.o. | 860.0 |
| rat | i.v. | 63.4 |
|  | s.c. | 125.6 |
|  | p.o. | 777.4 |

II - PHARMACOLOGICAL STUDY

This was carried out in the mouse, rabbit and rat.

1. Study in the mouse: mortality caused by low-pressure hypoxia 1.1 Method

An artificial altitude was created by placing the mouse in a sealed box and progressively reducing the pressure to 190 mm of mercury (equivalent to about 10,000 meters altitude) using a CEM-type pump, so that the desired altitude is obtained in 1 minute 10 seconds on average. A stopwatch is then started and the exact time when the chest movements cease is noted. Any mouse whose survival time is more than twice the average value noted in the corresponding "solvent control" series is regarded as protected.

The ED$_{50}$ was calculated from the percentage of "protected" mice using the graphical method indicated by LITCHFIELD and WILCOXON (J. Pharm. Exp. Ther., 1949, 96, 99–113).

1.2. Method of administration

The compound was administered by intraperitoneal route 20 minutes before the altitude is artifically created; whatever the dose, the volume injected was always equal to 20 ml/kg.

The effects were also examined after administration by oesophageal tube 60 minutes before the test, whilst the volume administered is always 20 ml/kg.

The entire study was carried out on adult male EOPS mice (4 to 5 weeks old) of the NMRI-Han strain, divided into random test groups after being fed only water for 18 hours.

1.3. Results

| 1.3.1 Administration by parenteral route | | |
|---|---|---|
| Doses mg/kg i.p. | Number of animals | Average and standard deviation |
| 2.5 | 12 | 88.4 ± 7.01 |
| 5.0 | 12 | 108.5 ± 20.22 |
| 10.0 | 12 | 155.7 ± 30.42 |
| 15 | 12 | 179.6 ± 32.07 |
| 20 | 12 | 275.4 ± 39.77 |
| 30 | 12 | 308.5 ± 35.65 |

-continued

1.3.2 Administration by oral route

| Doses mg/kg p.o. | Number of animals | Average and standard deviation |
|---|---|---|
| 50 | 20 | 122.6 ± 11.75 |
| 100 | 20 | 186.8 ± 25.70 |
| 150 | 20 | 179.7 ± 20.23 |
| 200 | 20 | 287.0 ± 25.58 |
| 250 | 20 | 306.5 ± 29.46 |
| 300 | 20 | 281.6 ± 30.61 |

1.3.3. Effective doese 50 ($ED_{50}$)

| Route | $ED_{50}$ |
|---|---|
| i.p. | 18.6 mg |
| p.o. | 246.8 mg |

1.4. Comments and conclusion

It appears that, in view of the test results obtained and regardless of the route of administration, the compound makes it possible to protect the mouse from the toxic effects of artificial altitude.

2. Study in the rabbit: effect on the development of cortical electrogenesis disrupted by the presence of a unilateral cerebral oedema in the unanaesthetised rabbit

2.1. Method 48 hours before use, the animal's cranium is exposed and stainless steel electrodes are screwed on so as to contact the dura mater on the frontal and occipital lobes on both sides of the median and transverse sutures. The electrocorticogram is recorded on a REEGA MINI HUIT TR electroencephalograph mounted transversely and longitudinally, whilst a 4th channel serves to record the electrocardiogram. Moreover, a flap of bone 7 to 10 mm in diameter was removed on one side, and this operation was not found, 48 hours later, to have caused any appreciable disruption of the electrical activity of the cortex.

An oedema was then produced by removing the dura mater and arachnoid; it usually takes the form of a hernia of the cortex. The treatment is then given and the electrocorticographic trace is monitored every hour during and after administration of the test products, then 24 and 48 hours later.

The action of the test products is assessed on the basic electrogenesis, particularly on the presence of slow waves and on the signs of cortical reactivity to two exteroceptive stimuli: a receptive stimulus (electrical tone lasting 2 seconds) and a nociceptive stimulation of the nerve endings in the skin by pinching the dorsal skin using KOCHER forceps.

The compounds are administered by either intravenous or intragastric route.

2.2 Administration by intravenous route

The compound has a therapeutic acitivity with regard to oedema symptoms from the point of view of both spontaneous electrogenesis and the duration of the alert reactions obtained during exteroceptive stimulation. The doses administered were 0.5 mg, 1 mg and 2 mg/kg.

2.3. Administration by intragastric route

In a dosage of 5 mg/kg, the compound significantly increases the value of the "R" index and this beneficial effect is of the order of 30%. In a dose of 10 mg/kg, a clear improvement in the value of the "R" index is obtained during the 8 hours following ingestion.

2.4. Conclusion

The compound has a beneficial effect on the development of electrogenesis in the cortex disrupted by the presence of a unilateral cerebral oedema in the unanaesthetised rabbit.

3. Study in the rat: Effect on a "spatial disorientation" syndrome

3.3.1. Method

This study was carried out using male rats of the Wistar AF-Han EOPS strains weighing about 160 g and about 6 to 7 weeks old.

After being guided through once by the experimenter, the rats are first of all subjected to 4 tests in 2 days in an aquatic labyrinth described by GIURGEA and MOURAVIEFFLESUISSE (J. Pharmacol. PARIS, 1972, 3, 1, 17–30).

On the 3rd day, the rats are subjected to a supramaximal electric shock delivered by a Neurovac controlled by a CRC OC 342 oscillograph; the electric shock has the following characteristics: 100 Hz, 0.5 ms, 1 second, 60 volts.

After passing through the labyrinth 20 minutes after the electric shock, the rats are given their treatment by oesophageal tube. Two tests are carried out 40 and 100 minutes after treatment, i.e. 60 and 120 minutes after the electric shock, and the time taken to pass through the labyrinth by each animal is timed; the number of errors is also noted.

3.2. Administering the compound

The rats are put on a diet of water for 18 hours after passing through for the 4th time. The compound is administered by intragastric route in a volume of 5 ml/kg.

3.3. Results

The following were noted:
time taken to leave the aquatic labyrinth;
average number of errors made in an effort to leave the labyrinth;
percentage of "normal" subjects, i.e. rats passing through the labyrinth with only 0–4 errors.

3.4 Results obtained

| | before electric shock | | | after electric shock | | | | | | | | |
|---|---|---|---|---|---|---|---|---|---|---|---|---|
| | | | | 20 minutes | | | 60 minutes | | | 120 minutes | | |
| dose/kg | 1 | 2 | 3 | 1 | 2 | 3 | 1 | 2 | 3 | 1 | 2 | 3 |
| 50 mg | 39 | 3.4 | 80 | 186 | 23.4 | 0 | 96 | 15.2 | 28 | 68 | 8.9 | 52 |
| 100 mg | 37 | 3.4 | 77 | 168 | 22.6 | 0 | 103 | 13.9 | 17 | 80 | 8.9 | 47 |

1 = average time taken in seconds
2 = average number of errors
3 = percentage of average animals
↓ gastric administration

3.5 Conclusion

It appears that, under the test conditions described, the compound administered by oral route accelerates the recovery of memory already instilled and affects the return of effective oxidative metabolism and thus of appropriate neuronal repolarisation.

The pharmacological study reported above clearly shows the value of the compounds according to the invention.

By virtue of this remarkable activity and the cerebral vasodilatory properties of the compounds of the invention, they may usefully be administered in human medicine.

They may advantageously be formulated for administration by oral route in the form of tablets, coated tablets, gelatine capsules and drops. They may also take the form of suppositories or injectable or drinkable solutions. Each dosage unit of 0.1 to 1 g may contain from 0.01 to 0.5 g of active ingredient.

Non-restrictive examples of pharmaceutical formulations of the medicine according to the invention will now be given:

1. TABLETS

| | |
|---|---|
| Compound according to inventon | 0.020 g |
| talc | 0.012 g |
| lactose | 0.035 g |
| magnesium stearate | 0.015 g |
| sugar q.s. for 1 tablet weighing | 0.200 g |

2. COATED TABLETS

Core

| | |
|---|---|
| Compound according to invention | 0.018 g |
| corn starch | 0.012 g |
| magnesium stearate | 0.018 g |
| talc | 0.020 g |
| sugar q.s. for 1 core weighing | 0.150 g |

Coating

| | |
|---|---|
| shellac | 0.02 g |
| talc | 0.20 g |
| carnauba wax | trace |
| titanium oxide | 0.005 g |
| sugar q.s. 1 for coated tablet ad | 0.250 g |

3. GELATINE CAPSULES

| | |
|---|---|
| Compound according to invention | 0.010 g |
| magnesium stearate | 0.036 g |
| talc | 0.005 g |
| for 1 gelatine capsule | |

4. INJECTABLE SOLUTION

| | |
|---|---|
| Compound according to invention | 0.025 g |
| isotonic solution | q.s. ad 5 ml |

By virtue of their properties, the compounds of the invention are indicated in cerebral circulatory insufficiency, the results of acute accidents of cerebral circulatory insufficiency, infections of vascular origin in ENT and ophthalmology, the results of cranial trauma, and following neurosurgical operations. The dosage depends on the weight of the patient and the intensity of the symptoms, but the average is twice a day, morning and night, at meal times, i.e. breakfast and dinner.

I claim:

1. Aspidospermidines of formula:

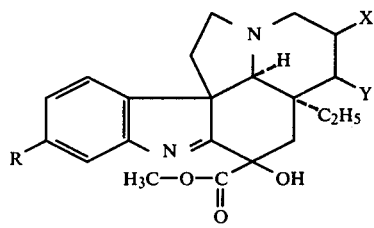

wherein R is hydrogen or methoxy, and X and Y are hydrogen or together represent a double bond between the carbon atoms to which they are attached.

2. 1,2-Dehydro-16-carbomethoxy-16 hydroxy-aspidospermidine.

3. The compound of claim 1, of the formula

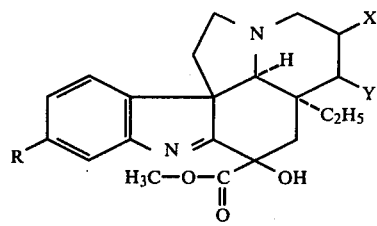

4. A process for preparing aspidospermidines of the formula:

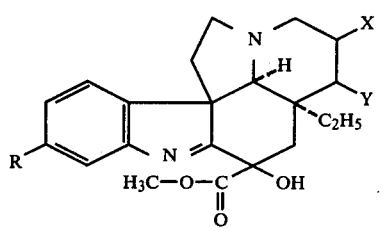

wherein R is hydrogen or methoxy, and X and Y are hydrogen or together represent a double bond between the carbon atoms to which they are attached, which comprises the step of converting the amines of the formula:

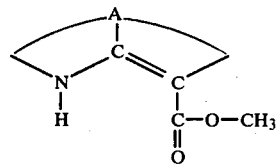

wherein A represents

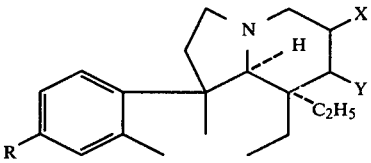

into their carbanions of the formula:

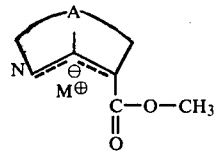

wherein M is an alkali metal or alkaline earth metal ion by reacting said amines in a solvent with about, but not less than; a stoichiometric amount of an alkali metal hydride, an alkali metal amide, an alkali metal alkylamide, an alkali metal alkylsilylamide, an alkali metal alkoxide or an alkaline earth metal alkoxide, the amide, alkylamide, alkysilylamide and alkoxide having up to 12 carbon atoms, so as to obtain a solution of the carbanion, oxidizing the carbanion by agitating its solution with pure oxygen or with a mixture of oxygen and an inert gas to obtain a solution of the hydroperoxide of the formula:

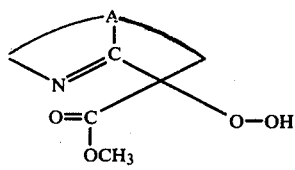

reducing said hydroperoxide by reacting it with a reducing agent selected from alkylphosphites, borohydrides or a metal salt in the lower state of oxidation, so as to obtain said aspidospermidine in a solution, and recovering said aspidospermidine from the last-mentioned solution.

5. The process of claim 4 wherein the carbanion is formed by heating the amine between $-80°$ and $+50°$ C. for 5 minutes to 12 hours.

6. The process of claim 4, wherein the oxidation is carried out at temperatures of from $-30°$ to $+50°$ C. for 5 minutes to 12 hours using oxygen under a pressure of from 1 to 10 Kg.cm$^{-2}$.

7. The process of claim 4, wherein the reduction is effected using a reducing agent selected from the alkyl ($C_1$-12) phosphite, the borohydrides and the salts in the lower state of oxidation, at temperatures of from $-30°$ to $+50°$ C.

* * * * *